(12) United States Patent
Sarnow et al.

(10) Patent No.: US 9,416,362 B2
(45) Date of Patent: Aug. 16, 2016

(54) METHODS AND COMPOSITIONS FOR REDUCING VIRAL GENOME AMOUNTS IN A TARGET CELL

(71) Applicant: The Board of Trustees of The Leland Stanford Junior University, Palo Alto, CA (US)

(72) Inventors: Peter Sarnow, Palo Alto, CA (US); Catherine L. Jopling, Beeston (GB); Alissa M. Lancaster, Portland, OR (US)

(73) Assignee: The Board of Trustees of The Leland Stanford Junior University, Palo Alto, CA (US)

(*) Notice: Subject to any disclaimer, the term of this patent is extended or adjusted under 35 U.S.C. 154(b) by 0 days.

(21) Appl. No.: 14/280,156

(22) Filed: May 16, 2014

(65) Prior Publication Data

US 2015/0005362 A1    Jan. 1, 2015

Related U.S. Application Data

(63) Continuation of application No. 13/529,694, filed on Jun. 21, 2012, now Pat. No. 8,759,312, which is a continuation of application No. 12/950,672, filed on Nov. 19, 2010, now Pat. No. 8,217,020, which is a continuation of application No. 11/953,705, filed on Dec. 10, 2007, now Pat. No. 7,838,504, which is a continuation of application No. 11/122,328, filed on May 3, 2005, now Pat. No. 7,307,067.

(60) Provisional application No. 60/568,358, filed on May 4, 2004.

(51) Int. Cl.
*C07H 21/04* (2006.01)
*C12N 15/113* (2010.01)
*C12N 15/11* (2006.01)

(52) U.S. Cl.
CPC .......... *C12N 15/1131* (2013.01); *C12N 15/111* (2013.01); *C12N 2310/113* (2013.01); *C12N 2310/14* (2013.01); *C12N 2310/141* (2013.01); *C12N 2310/321* (2013.01); *C12N 2320/50* (2013.01); *C12N 2330/10* (2013.01); *C12N 2770/24211* (2013.01)

(58) Field of Classification Search
None
See application file for complete search history.

(56) References Cited

U.S. PATENT DOCUMENTS

| | | | |
|---|---|---|---|
| 5,023,252 A | 6/1991 | Hseih et al. | |
| 5,610,050 A * | 3/1997 | Blum | A61K 31/70 435/238 |
| 5,922,687 A | 7/1999 | Mann et al. | |
| 5,985,310 A | 11/1999 | Castillo et al. | |
| 5,985,847 A | 11/1999 | Carson et al. | |
| 6,423,489 B1 | 7/2002 | Anderson | |
| 6,824,768 B2 | 11/2004 | Stalgis et al. | |
| 7,232,806 B2 | 6/2007 | Tuschi et al. | |
| 7,683,036 B2 | 3/2010 | Bennett | |
| 2002/0119122 A1 | 8/2002 | Stalgis et al. | |
| 2004/0175732 A1 | 9/2004 | Rana | |
| 2004/0229817 A1 | 11/2004 | Duggal et al. | |
| 2005/0227256 A1 | 10/2005 | Hutvagner et al. | |
| 2005/0261218 A1 * | 11/2005 | Esau et al. | 514/44 |
| 2005/0288245 A1 | 12/2005 | Sarnow et al. | |

FOREIGN PATENT DOCUMENTS

| | | |
|---|---|---|
| EP | 0699751 | 6/1996 |
| WO | 90/11092 | 10/1990 |
| WO | 95/30746 | 11/1995 |
| WO | 02/081494 | 10/2002 |
| WO | 2003/029459 | 4/2003 |
| WO | 03/070750 A2 | 8/2003 |
| WO | 2004/076622 | 9/2004 |
| WO | 2005/013901 A2 | 2/2005 |
| WO | 2005/013904 | 2/2005 |
| WO | 2005/013905 | 2/2005 |
| WO | 2007/027894 | 3/2007 |
| WO | 2007112753 | 10/2007 |
| WO | 2008091703 | 7/2008 |
| WO | 2009043354 | 4/2009 |

OTHER PUBLICATIONS

Pietschmann et al., "Tissue culture and animal models for hepatitis C virus." Clin Liver Dis 2003, 7:23-43.
Proprietor's Further Submissions filed Aug. 7, 2013, EP Patent No. 1747023, 11 pages.
Proprietor's Response to Opponent's submissions dated Dec. 20, 2013, Filed Feb. 14, 2014, EP Patent No. 1747023, 8 pages.
Proprietor's Response to Opposition, filed Jul. 23, 2012, EP Patent 1747023, 30 pages.
Protest of CA Application 2564503, Filed May 10, 2013, 41 pages.
Randall et al., "Cellular cofactors affecting hepatitis C virus infection and replication." PNAS U.S.A. 2007, 104 (31):12884-12889.
Recent Press Release of Santaris pharma a/s, "Santaris Pharma A/S to report new clinical data from miravirsen Phase 2a study to treat Hepatitis C in late-breaking oral presentation at the AASLD 2011 annual meeting." Oct. 3, 2011, 3 pages.
Reexamination of U.S. Pat. No. 7,838,504, filed Aug. 31, 2012. Control No. 95/002,129, 385 pages.
Re-examination Office Action issued Nov. 27, 2012, US Control No. 95/002,129; 26 pages.

(Continued)

*Primary Examiner* — Kimberly Chong
(74) *Attorney, Agent, or Firm* — Casimir Jones, S.C.; David Casimir

(57) ABSTRACT

Methods and compositions for reducing viral genome amounts in a target cell are provided. In the subject methods, the activity of a miRNA is inhibited in a manner sufficient to reduce the amount of viral genome in the target cell, e.g., by introducing a miRNA inhibitory agent in the target cell. Also provided are pharmaceutical compositions, kits and systems for use in practicing the subject methods. The subject invention finds use in a variety of applications, including the treatment of subjects suffering from a viral mediated disease condition, e.g., an HCV mediated disease condition.

7 Claims, 5 Drawing Sheets

(56) References Cited

OTHER PUBLICATIONS

Regulus Report of May 14, 2013, "Regulus Provides Update on 'Road to the Clinic' Strategy and Reports First Quarter 2013 Financial Results and Recent Highlights." pp. 1-2.
Regulus Reports Second Quarter 2013 Financial Results and Recent Highlights, Aug. 13, 2013.
Remington's Pharmaceutical Sciences, Mace Publ. Co Philadelphia, PA, 17th ed. (1985).
Response dated Sep. 17, 2007 in U.S. Appl. No. 10/909,125, Patent 7683036; 13 pages.
Response dated May 13, 2008, U.S. Appl. No. 10/909,125, Patent 7683036; 12 pages.
Response dated Aug. 4, 2009 in U.S. Appl. No. 10/909,125, Patent 7683036; 12 pages.
Roberts & Jopling, "Targeting Viral Infection by microRNA Inhibition." Genome Biology 2010, 11(201):1-4.
Santaris Annual Report 2010, pp. 1-54.
Santaris Pharma Press Release of 28th May 2008, "Santaris Pharam begins human clinical testing of world's first microRNA." pp. 1-2.
Saxena et al., "Small RNAs with Imperfect Match to Endogenous mRNA Repress Translation," J Biol Chem, 276(45), pp. 44312-44319 (2003).
Sempere et al., "Expression Profiling of Mammalian MicroRNAs Uncovers a Subset of Brain-Expressed MicroRNAs with Possible Roles in Murine and Human Neuronal Differentiation," Genome Biol, 5, pp. R13 (2004).
Shan et al, "Reciprocal Effects of MicroRNA-122 on Expression of Heme Oxygenase-1 and Hepatitis C Virus in Human Gepatocytes." Gastroenterology 133(4): 1166-1174, AGA Institue, Oct. 2007.
Shan et al, "Reciprocal Effects of MicroRNA-122 on Expression of HO-1 and HCV Genese in Human Hepatocytes." Hepatology 44(81): 256A-257A, Williams & Wilkins, Oct. 2006.
Statement of Grounds and Particulars filed by Santaris Mar. 8, 2012, Australian Application No. 2005240118, 16 pages.
Stenvang & Kauppinen, "MicroRNAs as targets for antisense-based therapeutics." Expert Opin Biol Ther. Jan. 2008; 8 (1):59-81.
Stenvang et al., "Inhibition of microRNA function by antimiR oligonucleotides." Silence. Jan. 9, 2012; 3(1):1.
Sumpter et al., "Regulating Intracellular Antiviral Defense and Permissiveness to Hepatitis C Virus RNA Replication through a Cellular RNA Helicase, RIG-I." J. Virology Mar. 2005, 2689-2699.
Sunkar et al., "Novel and Stress-Regulated MicroRNAs and Other Small RNAs from Arabidopsis," Plant Cell, 16, pp. 2001-2019 (2004).
Tang et al., "Genetic Immunization is A Simple Method for Eliciting an Immune Response," Nature, 356, pp. 152-154 (1992).
Taylor et al., "Hepatitis Delta Virus Replication and Liver Disease," RNA Biol, 1, pp. 106 (2004).
Tomari et al. "Perspective: machines for RNAi," Genes & Devel, 19, pp. 517-529 (2005).
Trujillo-Murillo et al., "Experimental models for hepatitis C virus (HCV); New opportunities for combating hepatitus C." Annals of Hepatitis 2004, 3(2): 54-62.
Provisional U.S. Appl. No. 60/493,990, filed Aug. 7, 2003, 64 pages.
Provisional U.S. Appl. No. 60/788,995, Filed Apr. 3, 2006, 60 pages.
Provisional U.S. Appl. No. 60/838,710, Filed Aug. 18, 2006.
Villanueva et al., "mIR-122 does not modulate the elongation phase of hepatitis C virus RNA synthesis in isolated replicase complexes." Antiviral Research 2010, 88:119-123.
Wengel, "LNA (Locked Nucleic Acid)." Antisense Drug Technology 2001, Edited by Stanley Crooke, Chapter 13, pp. 339-357.
Wolff et al., "Direct Gene Transfer into Mouse Muscle in Vivo," Science, 247, pp. 1465-1468 (1990).
Yekta et al., "MicroRNA-Directed Cleavage of HOXB8 mRNA," Science, 304:594-596 (2004).
Yi et al., "Adaptive mutations producing efficient replication of genotype 1a hepatitis C Virus RNA in normal Huh7 cells," J Virol, 78, pp. 7904-7915 (2004).
Zeng et al., "Sequence requirements for micro RNA processing and function in human cells." RNA 2003, 9:112-123.
Zeng et al., "MicroRNAs and Small Interfering RNAs Can Inhibit mRNA Expression by Similar Mechanisms," Proc. Natl. Acad. Sci. USA, 100(17), pp. 9779-9787 (2003).
Zhang et al., "High levels of foreign gene expression in hepatocytes after tail vein injections of naked plasmid DNA," Human Gene Ther, 10, pp. 1735-1737 (1999).
Zhang et al., "Long-term expression of human alpha1-antitrypsin gene in mouse liver achieved by intravenous administration of plasmid DNA using a hydrodynamics-based procedure," Gene Ther, 7, pp. 1344-1349 (2000).
Zhong et al., "Robust hepatitis C virus infection in vitro." PNAS 2008, 102(26):9294-9299.
Provisional U.S. Appl. No. 60/377,704, Filed May 3, 2002, Myers et al.
Provisional U.S. Appl. No. 60/568,358, Filed May 4, 2004, Sarnow et al.
"BioCryst Announces Promising Results from Preclinical Studies of BCX5191 for Hepatitis C." BusinessWire Feb. 12, 2012.
Abstract Entitled, " A Randomized, Double-blind, Placebo (PLB) Controlled Safety and Anti-viral Proof of Concept Study of Miravirsen (MIR), an Olignucleotide Targeting miR-122, in treatment Naive Patients with Genotype 1 (GT1) Chronic HCV Infection." AASLD 2011 Annual Meeting, 1 page.
Acsadi et al., "Direct gene transfer and expression into rat heart in vivo," New Biol, 3, pp. 71-81 (1991).
Agreement dated Feb. 24, 2010 between Regulus and GSK, 58 pages.
Altevogt et al., "Chimpanzees in Biomedical and Behavioral Research: Assessing the Necessity." Institute of Medicine and National Research Council, The National Academic Press 2010, pp. 47-50.
Available Options and Current Strategies, 2000 Stem Cells 18:307-319.
Bartenschlager, "Replication of hepatitis C Virus." J. General Virology 2000, 81:1631-1648.
Bartosch et al."Cell Entry of Hepatitis C Virus Requires a Set of Co-receptors That Include the CD81 Tetraspanin and the SR-B1 Scavenger Receptor." J. Biological Cehmistry 2003, 278(43):41624-41630.
Baskerville et al. "Microarray Profiling of MicroRNAs Reveals Frequent Coexpression with Neighboring miRNAs and Host Genes," (2005) RNA, 11, pp. 241-247.
Bennasser et al., "HIV-I Encoded Candidate Micro-RNAs and Their Cellular Targets," Retrovirol, 1, pp. 43 (2004).
Bhat et al- "2-O-Methoxyethyl/2'-Fluoro Modified Oligonucleotides Result in More Potent Inhibition of micro RNA-122 in vivo: A Target implicated in HCF Replication." Nucleic Acids Symposium Series No. 52 p. 69, Sep. 8, 2008.
Binder et al., "Replication Vesicles are Load- and Choke-Points in the Hepatitis C Virus Lifecycle." PloS Aug. 2013, 9(8):e1003561.
Boutla et al., "Developmental Defects by Antisense-Mediated Inactivation of Micro-RNAs 2 and 13 in Drosphilla and the Identification of Putative Target Genes," Nucleic Acids Research (2003) 31(17):4973-4980.
Brummelkamp, et al. "A system for stable expression of short interfering RNAs in mammalian cells" Science, vol. 296, pp. 550-553 (2002).
Bukh et al., "Mutations that permit efficient replication of hepatitis C virus RNA in Huh-7 cells prevent productive replication in chimpanzees." PNAS Oct. 29, 2002, 99(22):14416-14421.
Chang et al., "miR-122, a Mammalian Liver-Specific microRNA, is Processed from her mRNA and May Downregulate the High Affinity Catiionic Amino Acid Transporter CAT-1." RNA Biology 1: 106-113, Jul./Aug. 2004.
Chang et al., "Replication of the human hepatitis delta virus genome Is initiated in mouse hepatocytes following intravenous injection of naked DNA or RNA sequences," J Virol, 75, pp. 3469-3473 (2001).
Chen, "A microRNA as a Translational Repressor of APETALA2 in Arabidopsis Flower Development," Science, 303, pp. 2022-2025 (2004).

(56) References Cited

OTHER PUBLICATIONS

Chen, et al. "Viral virulence protein suppresses RNA silencing-mediated defense but upregulates the role of microrna in host gene expression" Plant Cell, vol. 16, No. 5, pp. 1302-13 (2004).
Crooke (2001) in Antisense Drug Technology, Chapter 1, Basic Principles of Antisense Technology, pp. 1-28 (Springer-Verlag).
Cullen, "Derivation and Function of Small Interfering RNAs and MicroRNAs," Virus Research (2004) 102:3-9.
Czech, "MicroRNAs as Therapeutic Targets." New England Journal of Medicine 2006, 354:1194-1195.
Davis et al., "Improved targeting of miRNA with antisense oligonucleotides." Nucleic Acids Research 2006, 34(8): 2294-2304.
Davis et al., "Potent inhibition of microRNA in vivo without degradation." Nucleic Acid Research 2009. 37(1): 70-77.
Dean et al., "Pharmacology of 2'-O-(2-Methoxy)ethyl-Modified Antisense Oligonucleotides." Antisense Drug Technology 2001, Edited by Stanley Crooke, Chapter 12, pp. 319-338.
Declaration of Dennis Chanter, Mar. 7, 2013, Australian Patent Application No. 2005240118 Opposition Proceedings, 76 pages.
Declaration of Dr. Susanna Obad, 4 pages, Sep. 2011.
Declaration of Eric James Gowans, Jul. 4, 2013, Australian Patent Application No. 2005240118 Opposition Proceedings, 128 pages.
Declaration of Morten Lindow, Dec. 11, 2013, in European Patent No. 1747023 opposition proceedings, 2 pages.
Declaration of Peter Sarnow, Feb. 26, 2014, Australian Patent Application No. 2005240118 Opposition Proceedings, Application 233 pages.
Declaration of Professor Brett Lindenbach, Mar. 11, 2013, Australian Patent Application No. 2005240118 Opposition Proceedings, 19 pages.
Declaration of Professor Robert Lanford, Mar. 19, 2013, Australian Opposition Proceedings, 21 pages.
Declaration of Susanna Obad, Feb. 26, 2013, Australian Patent Application No. 2005240118 Opposition Proceedings, 76 pages.
Declaration of Thomas Preiss dated Apr. 8, 2013, Australian Patent Application No. 2005240118 Opposition Proceedings, 128 pages.
Declaration of Victoria Mary Longshaw, Mar. 7, 2013, Australian Patent Application No. 2005240118 Opposition Proceedings, 16 pages.
Doench et al., "sIRNAs Can Function as miRNAs," Genes & Devel, 17:438-442 (2003).
Doench et al., "Specificity of MicroRNA Target Selection in Translational Repression," Genes & Devel, 504-511 (2004).
Elmen et al, "LNA-mediated microRNA silencing in non-human primates." Nature 2008, 452: 896-900.
Elvidge, Susan, "Troubled BioCryst dumps HCV preclinical program." Fierce Biotech Research www. Fiercebiotechresearch.com, Jan. 29, 2013.
Enserink, "RNA Silencer Shows Promise for Hepatitis C." Science Now, Dec. 3, 2009, www.sciencemag.org, 2 pages.
Esau et al., "Identification of microRNAs Involved in Adipocyte Development Using Second-Generation Antisense Oligonucleotides in an in Vitro AdiopocyteDifferentiation Model." Keystone Symposia: siRNAs and miRNAs. Apr. 14-19, 2004, Abstract #117.
Esau et al., "Inhibition of microRNA with antisense oligonucleotides." Methods 2008; 44:55-60.
Esau et al., "miR-122 regulation of lipid metabolism revealed by in vivo antisense targeting." Cell Metabolism, Feb. 2006, 3:87-98.
Feld & Hoofnagle, "Mechanism of action of interferon and ribavirin in treatment of hepatitis C." Nature 436:967-972, Nature Publishing Group, England (Aug. 18, 2005).
Friebe et al., "Sequences in the 5' Nontranslated Region of Hepatitis C Virus Required for RNA Replication," J Virol, 75(24), pp. 12047-12057 (2001).
Furth et al., "Gene transfer into somatic tissues by jet injection," Anal Biochem, 205, pp. 365-368 (1992).
Geary et al., "Pharmacokinetics of Phosphorothioate antisense oligodeoxynucleotides." Curr Opin. Investig. Drugs 2001, 2(4):562-573.

Guidance for Industry Antiviral Product Development—Conducting and submitting Virology Studies to the Agency—US Department of Health and Human Services, Jun. 2006, 17 pages.
Hickman et al., "Gene expression following direct injection of DNA into liver," Human Gene Ther, 5, pp. 1477-1483 (1994).
Holmlund, "Applying Antisense Technology: Affinitak and other Antisense Oligonucleotides in Clinical Development." Ann. NY Acad. Sci. 2003, 1002:244-251.
Horscroft et al., "Replicon cell culture system as a valuable tool in antiviral drug discovery against hepatitis C virus." Antiviral Chemistry & Chemotherapy 2005, 16:1-12.
Hutvagner et al., "Sequence-Specific Inhibition of Small RNA Function." PloS Biology Apr. 2004, 2(4): 465-475.
Hutvagner et al., "A MicroRNA in a Multiple-Turnover RNAi Enzyme Complex," (2002) Science, 297:2056-2060.
Hutvagner et al., "Sequence-Specific Inhibition of Small RNA Function," PLoS Biology, 2, pp. 0465-0475 (2004).
Ikeda et al., "Selectable Subgenomic and Genome Length Dicistronic RNAs Derived from an Infectious Molecular Clone of the HCV-N Strain of Hepatitis C Virus Replicate Efficiently in Cultured Huh7 Cells," J Virol, 76, pp. 2997-3006 (2002).
International Search Report, PCT/US2005/015264, dated Nov. 21, 2005, 5 pages.
Jackson and Linsley, "The Therapeutic Potential of microRNA modulation." www.discoverymedicine.com, May 5, 2010.
Janssen et al., "Treatment of HCV Infection by Targeting MicroRNA." New England J of Medicine, May 2, 2013, 368 (18):1685-94.
Jen et al., "ression of Gene Expression by Targeted Disruption of Messenger RNA: Available Options and Current Strategies." Stem Cells Sep. 2000, 18(5): 307-319.
Jepsen et al. "Locked Nucleic Acid: A Potent Acid Analog in Therapeutics and Biotechnology." Oligonucleotides 2004, 14:130-146.
Ji et al., "Coordinated assembly of human translation initiation complexes by the hepatitis C virus internal ribosome entry site RNA," Proc Natl Acad. Sci. USA, 101, pp. 16990-16995 (2004).
Jin et al., "Biochemical and genetic interaction between the fragile X mental retardation protein and the microRNA pathway." Nat Neurosci 2004, 7:113-117.
John et al., "Human MicroRNA Targets," PLoS Biology, 2(11):1862-1879 (2004).
Jopling et al., "Liver-Specific microRNA122 regulates hepatitis C Viral RNA Abundance." Cold Spring Harbor Laboratory Meeting 'Translational Control', Cold Spring Harbor USA, Sep. 7-12, 2004, p. 124.
Jopling et al., "Position-Dependent Function for a Tandem MicroRNA miR-122-Binding Site Located in the Hepatitis C Virus RNA Genome." Cell Host & Microbe 2008, 4:77-85.
Jopling et al., "Targeting microRNA-122 to treat Hepatitis C Virus Infection." Viruses 2010, 2:1382-1393.
Jopling et al.; Abstract of papers presented at the meeting on translational control, Cold Spring Harbor Conference; Sep. 7-12, 2004.
Jopling, "Regulation of Hepatitis C virus by microRNA-122" Biochemical Society Transactions 2008, 36(6): 1220-1223.
Jopling, et al. "Modulati on of hepatitis C virus RNA abundance by a liver-specific microRNA" Science, vol. 309, No. 5740, Sep. 1, 2005, pp. 1577-1581.
Kassachau et al., "P1/HC-Pro, A Viral Suppressor of RNA Silencing, Interferes with Arabidopsis Development and miRNA Function," Development Cell (2003) 4:205-217.
Khan et al. "Transfection of small RNAs globally perturbs gene regulation by endogenous microRNAs." Nature Biotechnology, Advanced Online Publication May 24, 2009, 9 pages.
Krutzfeldt et al., "Silencing of microRNAs in vivo with 'antagomirs'" Nature 2005, 438:685-689.
Krutzfeldt et al.. "Specificity, duplex degradation and subcellular localization of antagomirs." Nuclic Acids Research 2007, 35(9):2885-2895.
Lagos-Quintana, et al., "Identification of Tissue-Specific MicroRNAs from Mouse," Curr Biol, 12:736-739, including Supplementary Material, pp. S1-S15 (2002).
Lanford et al., "Antiviral Effect and Virus-Host Interactions in Response to Alpha Interferon, Gamma Interferon, Poly(I)-Poly( C ),

(56) References Cited

OTHER PUBLICATIONS

Tumor Necrosis Factor Alpha, and Ribavirin in Hepatitis C Virus Subgenomic Replicons." Journal of Virology, Jan. 2003, 1092-1104.

Lanford et al., "The Chimpanzee Model of Hepatitis C Virus Infections." ILAR Journal 2001, 42(2):117-126.

Lanford et al., "Therapeutic Silencing of MicroRNA-122 in Primates with Chronic Hepatitis C Virus Infection." Science 2010, 327:198-201.

Levin, "A review of issues in the pharmacokinetics and toxicology of phosphorothioate antisense oligonucleotides." Biochimica et Biophysica Acta. 1999, 1486:69-84.

Lewis et al., "Conserved Seed Pairing, Often Flanked by Adenosines, Indicates that Thousands of Human Genes are MicroRNA Targets," Cell, 120, pp. 15-20 (2005).

Lewis, et al., "Prediction of Mammalian MicroRNA Targets," Cell, 115, pp. 787-798 (2003).

Lim, et al., "Microarray Analysis Shows that Some MicroRNAs Downregulate Large Numbers of Target mRNAs," Nature, 433:769-773 (2005).

Lindenbach, "Complete Replication of Hepatitis C Virus in Cell Culture." Science 2005, 309:623-626.

Liu et al., "Hydrodynamics-based transfection in animals by systemic administration of plasmid DNA," Gene Ther 6, pp. 1258-1266 (1999).

Machlin et al., "Masking the 5' terminal nucleotides of the hepatitis C virus genome by an unconventional microRNA-target RNA complex." PNAS Feb. 22, 2011, 108 (8): 3193-3198.

Lu et al, "Delivering siRNA in vivo for functional genomics and novel therapeutics." In RNA Interference Technology 2005, Appasani Ed. p. 303 (Cambridge University).

McCaffrey, et al. "RNA interference V in adult mice" Nature, vol. 418, No. 6893, Jul. 4, 2002, pp. 38-39.

McManus et al., "MicroRNAs and cancer." Semin Cancer Biol. Aug. 2003; 13(4):253-8. Abstract Only, PMID: 14563119.

Meister et al. "Sequence-specific inhibition of microRNA-and SiRNA-induced RNA silencing", (2004) RNA 10:544-550.

Nature Publication—Supplementary Information for Elmen et al, "LNA-mediated microRNA silencing in non-human primates." Nature 2008, 452: 896-900.

Norman & Sarnow, "Hepatitis C Virus' Achilles' heel—Dependence on liver-specific microRNA miR-122." Cell Research 2010, 20:247-249.

Norman & Sarnow, "Modulation of Hepatitis C Virus RNA Abundance and the Isoprenoid Biosynthesis Pathway by MicroRNA miR-122 Involves Distinct Mechanisms." J Virology Jan. 2010, 84(1):666-670.

Olsen et al., "The lin-4 Regulatory RNA Controls Developmental Timing in Caenorhabditis Elegans by Blocking LIN-14 Protein Synthesis After the Initiation of Translation," Dev Biol, 216:671-680 (1999).

Opponent's Further Submissions Filed Dec. 20, 2013 in EP Patent 1747023, 17 pages.

Opponent's Reply Submissions filed Apr. 19, 2013, EP Patent No. 1747023, 39 pages.

Opposition of AU Patent Application No. 2005240118 filed Dec. 8, 2011, 3 pages.

Opposition of EP Patent 1747023 filed Oct. 4, 2011; 103 pages.

Otto et al., "The pathway of HCV IRES-mediated translation initiation," Cell, 119, pp. 369-380 (2004).

Pavio et al., "The hepatitis C Virus persistence: how to evade the immune system." J. Biosci 2003, 28(3): 287-304.

Pestova et al., "A prokaryotic-like mode of cytoplasmic eukaryotic ribosome binding to the initiation codon during internal translation initiation of hepatitis C and classical swine fever virus RNAs," Genes Dev, 12, pp. 67-83 (1998).

Pfeffer et al., "Identification of Virus-Encoded MicroRNAs," Science (2004), 304(5671):734-736.

\* cited by examiner

SEQUENCE LISTING

```
<160> NUMBER OF SEQ ID NOS: 35

<210> SEQ ID NO 1
<211> LENGTH: 20
<212> TYPE: RNA
<213> ORGANISM: Homo sapiens

<400> SEQUENCE: 1
```

-continued ugauggggc gacacuccac                                          20

<210> SEQ ID NO 2
<211> LENGTH: 25
<212> TYPE: RNA
<213> ORGANISM: Homo sapiens

<400> SEQUENCE: 2
ugaagguugg gguaacacuc cggcc                                   25

<210> SEQ ID NO 3
<211> LENGTH: 20
<212> TYPE: RNA
<213> ORGANISM: Homo sapiens

<400> SEQUENCE: 3 auuggggcg acacuccacc                                          20

<210> SEQ ID NO 4
<211> LENGTH: 25
<212> TYPE: RNA
<213> ORGANISM: Homo sapiens

<400> SEQUENCE: 4
ugaacgggga gcuaaacacu ccagg                                   25

<210> SEQ ID NO 5
<211> LENGTH: 20
<212> TYPE: RNA
<213> ORGANISM: Homo sapiens

<400> SEQUENCE: 5
aauaggggcg acacuccgcc                                         20

<210> SEQ ID NO 6
<211> LENGTH: 28
<212> TYPE: RNA
<213> ORGANISM: Homo sapiens

<400> SEQUENCE: 6
uagagcggca cacuaggu acacucca                                  28

<210> SEQ ID NO 7
<211> LENGTH: 20
<212> TYPE: RNA
<213> ORGANISM: Homo sapiens

<400> SEQUENCE: 7
uacgaggcga cacuccacca                                         20

<210> SEQ ID NO 8
<211> LENGTH: 25
<212> TYPE: RNA
<213> ORGANISM: Homo sapiens

<400> SEQUENCE: 8
ugagcuggua agauaacacu ccauu                                   25

<210> SEQ ID NO 9
<211> LENGTH: 20
<212> TYPE: RNA
<213> ORGANISM: Homo sapiens

```
<400> SEQUENCE: 9
uaugagagca acacuccacc                                          20

<210> SEQ ID NO 10
<211> LENGTH: 25
<212> TYPE: RNA
<213> ORGANISM: Homo sapiens

<400> SEQUENCE: 10
uaggcagcuu aacacuccga ccuua                                    25

<210> SEQ ID NO 11
<211> LENGTH: 20
<212> TYPE: RNA
<213> ORGANISM: Homo sapiens

<400> SEQUENCE: 11
uauuggggcg acacuccacc                                          20

<210> SEQ ID NO 12
<211> LENGTH: 25
<212> TYPE: RNA
<213> ORGANISM: Homo sapiens

<400> SEQUENCE: 12
uaggcuggga gcuaaacacu ccaua                                    25

<210> SEQ ID NO 13
<211> LENGTH: 20
<212> TYPE: RNA
<213> ORGANISM: Homo sapiens

<400> SEQUENCE: 13 aaugggggcga cacuccacca                                         20

<210> SEQ ID NO 14
<211> LENGTH: 27
<212> TYPE: RNA
<213> ORGANISM: Homo sapiens

<400> SEQUENCE: 14
uagacaggga gcauaaauaa cacucca                                  27

<210> SEQ ID NO 15
<211> LENGTH: 31
<212> TYPE: RNA
<213> ORGANISM: Homo sapiens

<400> SEQUENCE: 15
agacacaaac accauuguca cacuccacag c                             31

<210> SEQ ID NO 16
<211> LENGTH: 30
<212> TYPE: RNA
<213> ORGANISM: Homo sapiens

<400> SEQUENCE: 16
cacguuaaaa ccauacgcac uacgaaaccc                               30

<210> SEQ ID NO 17
<211> LENGTH: 31
<212> TYPE: RNA
<213> ORGANISM: Homo sapiens
```

```
<400> SEQUENCE: 17
cuaaaacuau acaaccuacu accucauccc a                               31

<210> SEQ ID NO 18
<211> LENGTH: 23
<212> TYPE: RNA
<213> ORGANISM: Homo sapiens

<400> SEQUENCE: 18
acaaacacca uugucacacu cca                                        23

<210> SEQ ID NO 19
<211> LENGTH: 23
<212> TYPE: RNA
<213> ORGANISM: Homo sapiens

<400> SEQUENCE: 19
ugaacgggga gcuaaacacu cca                                        23

<210> SEQ ID NO 20
<211> LENGTH: 23
<212> TYPE: RNA
<213> ORGANISM: Homo sapiens

<400> SEQUENCE: 20
uggaguguga cauggguguu ugu                                        23

<210> SEQ ID NO 21
<211> LENGTH: 23
<212> TYPE: RNA
<213> ORGANISM: Homo sapiens

<400> SEQUENCE: 21
ugcaguguga cauggguguu ugu                                        23

<210> SEQ ID NO 22
<211> LENGTH: 23
<212> TYPE: RNA
<213> ORGANISM: Homo sapiens

<400> SEQUENCE: 22
aaacgccauu aucacacuaa aua                                        23

<210> SEQ ID NO 23
<211> LENGTH: 23
<212> TYPE: RNA
<213> ORGANISM: Homo sapiens

<400> SEQUENCE: 23
acaaacacca uugucacacu cca                                        23

<210> SEQ ID NO 24
<211> LENGTH: 22
<212> TYPE: DNA
<213> ORGANISM: Homo sapiens

<400> SEQUENCE: 24
ttaaggcacg cggtgaatgc ca                                         22

<210> SEQ ID NO 25
<211> LENGTH: 23
<212> TYPE: RNA
```

<213> ORGANISM: Homo sapiens

<400> SEQUENCE: 25
acaaacacca uugucacacu cca                                          23

<210> SEQ ID NO 26
<211> LENGTH: 238
<212> TYPE: RNA
<213> ORGANISM: Hepatitis C virus

<400> SEQUENCE: 26
cuccccaacc gaugaagguu gggguaaaca cuccggccuc uuaagccauu uccuguuuuu    60
uuuuuuuuuu uuuuuuuuuu uuuccccccc cccccccccc cccccccccc cccccccccc   120
cccccccccc cccccccaau gguggcucca ucuuagcccu agucacggcu agcugugaaa   180
gguccgugag ccgcaugacu gcagagagug cugauacugg ccucucugca gaucaugu     238

<210> SEQ ID NO 27
<211> LENGTH: 129
<212> TYPE: RNA
<213> ORGANISM: Hepatitis C virus

<400> SEQUENCE: 27
gccagccccc ugauggggggg acaccuccacc auagaucacu ccccugugag gaucuacugu    60
cuucacgcag aaagcgucua gccauggcgu uaguaugagu gucgugcagc cuccaggacc   120
cccccucccc                                                         129

<210> SEQ ID NO 28
<211> LENGTH: 23
<212> TYPE: RNA
<213> ORGANISM: Homo sapiens

<400> SEQUENCE: 28
auaaaucaca cuauuaccgc aaa                                          23

<210> SEQ ID NO 29
<211> LENGTH: 23
<212> TYPE: RNA
<213> ORGANISM: Homo sapiens

<400> SEQUENCE: 29
auaaaucaca cuauuaccgc aaa                                          23

<210> SEQ ID NO 30
<211> LENGTH: 24
<212> TYPE: RNA
<213> ORGANISM: Hepatitis C virus

<400> SEQUENCE: 30
augaagguug ggguaaacac uccg                                         24

<210> SEQ ID NO 31
<211> LENGTH: 24
<212> TYPE: RNA
<213> ORGANISM: Hepatitis C virus

<400> SEQUENCE: 31
augaagguug ggguaaacag aggg                                         24

<210> SEQ ID NO 32
<211> LENGTH: 17

```
<212> TYPE: RNA
<213> ORGANISM: Hepatitis C virus

<400> SEQUENCE: 32 auggggcga cacucca                                                    17

<210> SEQ ID NO 33
<211> LENGTH: 17
<212> TYPE: RNA
<213> ORGANISM: Hepatitis C virus

<400> SEQUENCE: 33 auggggcga cagagga                                                    17

<210> SEQ ID NO 34
<211> LENGTH: 17
<212> TYPE: RNA
<213> ORGANISM: Hepatitis C virus

<400> SEQUENCE: 34 auggggcga cacagca                                                    17

<210> SEQ ID NO 35
<211> LENGTH: 17
<212> TYPE: RNA
<213> ORGANISM: Hepatitis C virus

<400> SEQUENCE: 35 auggggcga cacugca                                                    17
```

US 9,416,362 B2

METHODS AND COMPOSITIONS FOR REDUCING VIRAL GENOME AMOUNTS IN A TARGET CELL

CROSS-REFERENCE TO RELATED APPLICATIONS

Pursuant to 35 U.S.C. §119 (e), this application claims priority to the filing date of the U.S. Provisional Patent Application Ser. No. 60/568,358 filed May 4, 2004; the disclosure of which is herein incorporated by reference.

STATEMENT REGARDING FEDERALLY SPONSORED RESEARCH OR DEVELOPMENT

This invention was made with Government support under AI047365 awarded by the National Institutes of Health. The Government has certain rights in this invention.

INTRODUCTION

1. Background of the Invention

Viral infections are a continuing medical problem because, like any rapidly dividing infectious agent, there are continuing mutations that help some subpopulations of viruses continue to be resistant to current treatment regimens. Many virally-based diseases do not have effective anti-viral treatments, because such treatments address the symptoms of the viral disease and not the root cause of the disease. There is a need in the art to discover and develop new anti-viral therapies.

MicroRNAs (miRNAs) are a class of small RNA molecules, approximately 21-22 nts in length, that have been detected in many plant and animal species. Even certain animal viral RNA genomes have been found to encode miRNAs. Cloning efforts and computational predictions have indicated that there are likely to be over 200 miRNA-encoding genes in humans, which can regulate approximately 1000-2000 mRNAs. Certain miRNAs are expressed ubiquitously, whereas others are expressed in a highly tissue-specific manner. For example, miR-122 was noted to be specifically expressed in the liver, where it constitutes 70% of the total miRNA population.

2. Relevant Literature

Tomari & Zamore, Genes Dev. 19, 517 (2005); Bennasser, et al., Retrovirology 1, 43 (2004); Pfeffer et al., Science 304, 734 (2004); Baskerville & Bartel, RNA 11, 241 (2005); John et al., PLoS Biol. 2, e363 (2004); Lim et al., Nature 433, 769 (2005); Hutvagner, Science 297, 2056 (2002); Yekta, et al., Science 304, 594 (2004); Chen, Science 303, 2022 (2004); Doench, et al., Genes Dev. 17, 438 (2003); Doench & Sharp, Genes Dev. 18, 504 (2004); Olsen, Dev. Biol. 216, 671 (1999); Saxena & Dutta, J. Biol. Chem. 278, 44312 (2003); Zeng, et al., Proc. Nat'l. Acad. Sci. USA 100, 9779 (2003); Lagos-Quintana et al., Curr. Biol. 12, 735 (2002); Sempere et al., Genome Biol. 5, R13 (2004); Chang, et al., RNA Biology 1, 106 (2004); Lewis, et al., Cell 120, 15 (2005); Lewis et al., Cell 115, 787 (2003); Ikeda, et al., J. Virol. 76, 2997 (2002). Friebe, et al., J. Virol. 75, 12047 (2001); Sunkar, et al., Plant Cell 16, 2001 (2004).

SUMMARY OF THE INVENTION

Methods and compositions for reducing viral genome amounts in a target cell are provided. In the subject methods, the activity of a miRNA is inhibited in a manner sufficient to reduce the amount of viral genome in the target cell, e.g., by introducing a miRNA inhibitory agent in the target cell. Also provided are pharmaceutical compositions, kits and systems for use in practicing the subject methods. The subject invention finds use in a variety of applications, including the treatment of subjects suffering from a viral mediated disease condition, e.g., an HCV mediated disease condition.

BRIEF DESCRIPTION OF THE FIGURES

—FIG. 5A shows structures of miR-122wt duplex and miR-122Mc duplex.

DESCRIPTION OF THE SPECIFIC EMBODIMENTS

Figure 1A:
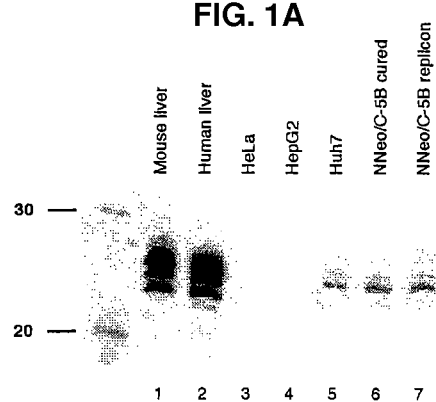
FIGS. 1A-1C. miR-122 is expressed in Huh7 cells and has two predicted binding sites in the HCV genome. (A) Northern blot analysis of miR-122 expression in total RNA extracted from mouse and human liver, and HeLa, HepG2 and naive, cured and replicon Huh7 cells. (B) Sequence of miR-122 with the seed sequences surrounded by a box. (C) Secondary structure of the 3' and 5' noncoding regions of the HCV genotype 1a strain H77c, with predicted miR-122 binding sites indicated. The seed matches are enclosed in boxes.

Methods and compositions for reducing viral genome amounts in a target cell are provided. In the subject methods, the activity of a miRNA is inhibited in a manner sufficient to reduce the amount of viral genome in the target cell, e.g., by introducing a miRNA inhibitory agent in the target cell. Also provided are pharmaceutical compositions, kits and systems for use in practicing the subject methods. The subject invention finds use in a variety of applications, including the treatment of subjects suffering from a viral mediated disease condition, e.g., an HCV mediated disease condition.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Methods recited herein may be carried out in any order of the recited events which is logically possible, as well as the recited order of events.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As summarized above, the subject invention provides methods and compositions reducing the amount of a target viral genome in a target cell. In further describing the subject invention, the subject methods are described first in greater detail, followed by a review of various representative applications in which the subject invention finds use as well as kits that find use in practicing the subject invention.

Methods

As indicated above, the subject invention provides methods of reducing the amount of a target viral genome in a target cell, where the target cell may be present in vitro or in vivo. By "reducing the amount of" is meant that the level or quantity of the target viral genome in the target cell is reduced by at least about 2-fold, usually by at least about 5-fold, e.g., 10-fold, 15-fold, 20-fold, 50-fold, 100-fold or more, as compared to a control, i.e., an identical target cell not treated according to the subject methods.

In practicing the subject methods, an effective amount of a miRNA (microRNA) inhibitory agent is introduced into the target cell, where any convenient protocol for introducing the agent into the target cell may be employed. The miRNA inhibitory agent is an agent that inhibits the activity of a target miRNA in the target cell. The target miRNA is a miRNA whose presence is associated with viral genome replication and abundance in the target cell. As is known in the art, miRNAs are single stranded RNA molecules that range in length from about 20 to about 25 nt, such as from about 21 to about 24 nt, e.g., 22 or 23 nt. The target miRNAs may or may not be completely complementary to a region of the same length as the miRNA in the target viral genome. If not completely complementary, the miRNA and its corresponding target viral genome are at least substantially complementary, such that the amount of mismatches present over the length of the miRNA, (ranging from about 20 to about 25 nt) will not exceed about 8 nt, and will in certain embodiments not exceed about 6 or 5 nt, e.g., 4 nt.

By miRNA inhibitory agent is meant an agent that inhibits the activity of the target miRNA. The inhibitory agent may inhibit the activity of the target miRNA by a variety of different mechanisms. In certain embodiments, the inhibitory agent is one that binds to the target miRNA and, in doing so, inhibits its activity.

Representative miRNA inhibitory agents include, but are not limited to: antisense oligonucleotides, such as the specific antisense oligonucleotides reported in the experimental section below, and the like. Other agents of interest include, but are not limited to: Naturally occurring or synthetic small molecule compounds of interest include numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Such molecules may be identified, among other ways, by employing appropriate screening protocols.

Also of interest in certain embodiments are RNAi agents. In representative embodiments, the RNAi agent targets the precursor molecule of the microRNA, known as pre-microRNA molecule. By RNAi agent is meant an agent that modulates expression of microRNA by a RNA interference mechanism. The RNAi agents employed in one embodiment of the subject invention are small ribonucleic acid molecules (also referred to herein as interfering ribonucleic acids), i.e., oligoribonucleotides, that are present in duplex structures, e.g., two distinct oligoribonucleotides hybridized to each other or a single ribooligonucleotide that assumes a small hairpin formation to produce a duplex structure. By oligoribonucleotide is meant a ribonucleic acid that does not exceed about 100 nt in length, and typically does not exceed about 75 nt length, where the length in certain embodiments is less than about 70 nt. Where the RNA agent is a duplex structure of two distinct ribonucleic acids hybridized to each other, e.g., an siRNA (such as d-siRNA as described in copending application Ser. No. 60/377,704; the disclosure of which is herein incorporated by reference), the length of the duplex structure typically ranges from about 15 to 30 bp, usually from about 15 to 29 bp, where lengths between about 20 and 29 bps, e.g., 21 bp, 22 bp, are of particular interest in certain embodiments. Where the RNA agent is a duplex structure of a single ribonucleic acid that is present in a hairpin formation, i.e., a shRNA, the length of the hybridized portion of the hairpin is typically the same as that provided above for the siRNA type of agent or longer by 4-8 nucleotides. The weight of the RNAi agents of this embodiment typically ranges from about 5,000 daltons to about 35,000 daltons, and in many embodiments is at least about 10,000 daltons and less than about 27,500 daltons, often less than about 25,000 daltons.

In certain embodiments, instead of the RNAi agent being an interfering ribonucleic acid, e.g., an siRNA or shRNA as described above, the RNAi agent may encode an interfering ribonucleic acid, e.g., an shRNA, as described above. In other words, the RNAi agent may be a transcriptional template of the interfering ribonucleic acid. In these embodiments, the transcriptional template is typically a DNA that encodes the interfering ribonucleic acid. The DNA may be present in a vector, where a variety of different vectors are known in the art, e.g., a plasmid vector, a viral vector, etc.

As indicated above, the miRNA inhibitory agent can be introduced into the target cell(s) using any convenient protocol, where the protocol will vary depending on whether the target cells are in vitro or in vivo.

Where the target cells are in vivo, the miRNA agent can be administered to the host using any convenient protocol. In embodiments where the inhibitory agent is a nucleic acid, the protocol employed is typically a nucleic acid administration protocol, where a number of different such protocols are known in the art. The following discussion provides a review of representative nucleic acid administration protocols that may be employed. The nucleic acids may be introduced into tissues or host cells by any number of routes, including viral infection, microinjection, or fusion of vesicles. Jet injection may also be used for intra-muscular administration, as described by Furth et al. (1992), *Anal Biochem* 205:365-368. The nucleic acids may be coated onto gold microparticles, and delivered intradermally by a particle bombardment device, or "gene gun" as described in the literature (see, for example, Tang et al. (1992), *Nature* 356:152-154), where gold microprojectiles are coated with the DNA, then bombarded into skin cells. Expression vectors may be used to introduce the nucleic acids into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

For example, the inhibitory agent can be fed directly to, injected into, the host organism containing the target gene. The agent may be directly introduced into the cell (i.e., intracellularly); or introduced extracellularly into a cavity, interstitial space, into the circulation of an organism, introduced orally, etc. Methods for oral introduction include direct mixing of RNA with food of the organism. Physical methods of introducing nucleic acids include injection directly into the cell or extracellular injection into the organism of an RNA solution. The agent may be introduced in an amount which allows delivery of at least one copy per cell. Higher doses (e.g., at least 5, 10, 100, 500 or 1000 copies per cell) of the agent may yield more effective inhibition; lower doses may also be useful for specific applications.

In certain embodiments, a hydrodynamic nucleic acid administration protocol is employed. Where the agent is a ribonucleic acid, the hydrodynamic ribonucleic acid administration protocol described in detail below is of particular interest. Where the agent is a deoxyribonucleic acid, the hydrodynamic deoxyribonucleic acid administration protocols described in Chang et al., J. Virol. (2001) 75:3469-3473; Liu et al., Gene Ther. (1999) 6:1258-1266; Wolff et al., Science (1990) 247: 1465-1468; Zhang et al., Hum. Gene Ther. (1999) 10:1735-1737: and Zhang et al., Gene Ther. (1999) 7:1344-1349; are of interest.

Additional nucleic acid delivery protocols of interest include, but are not limited to: those described in U.S. patents of interest include U.S. Pat. Nos. 5,985,847 and 5,922,687 (the disclosures of which are herein incorporated by reference); WO/11092; Acsadi et al., New Biol. (1991) 3:71-81; Hickman et al., Hum. Gen. Ther. (1994) 5:1477-1483; and Wolff et al., Science (1990) 247: 1465-1468; etc.

Depending n the nature of the inhibitory agent, the active agent(s) may be administered to the host using any convenient means capable of resulting in the desired reduction of target viral genome amount or load in the target cell. Thus, the agent can be incorporated into a variety of formulations for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. As such, administration of the agents can be achieved in various ways, including oral, buccal, rectal, parenteral, intraperitoneal, intradermal, transdermal, intracheal, etc., administration.

In pharmaceutical dosage forms, the agents may be administered alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Those of skill in the art will readily appreciate that dose levels can vary as a function of the specific compound, the nature of the delivery vehicle, and the like. Preferred dosages for a given compound are readily determinable by those of skill in the art by a variety of means.

Introduction of an effective amount of an RNAi agent into a mammalian cell as described above results in a modulation of target gene(s) expression, e.g., a reduction of target gene(s) expression, as described above.

The above described methods work in any mammalian cell, where representative mammal cells of interest include, but are not limited to cells of: ungulates or hooved animals, e.g., cattle, goats, pigs, sheep, etc.; rodents, e.g., hamsters, mice, rats, etc.; lagomorphs, e.g., rabbits; primates, e.g., monkeys, baboons, humans, etc.; and the like.

The compositions may be advantageously combined and/or used in combination and/or alternation with other antiviral agents which are either therapeutic or prophylactic agents, and different from the subject compounds. The compositions may also be advantageously combined and/or used in combination with agents that treat conditions often associated with the viral infections that are sensitive to the present compounds, such as anti-HCV agents or immunosuppressive agents. In certain embodiments, administration in conjunction with the subject compositions enhances the efficacy of such agents. Accordingly, the present compounds, when combined or administered in combination with other antiviral agents, can be used in certain embodiments in dosages which are less than the expected amounts when used alone, or less than the calculated amounts for combination therapy.

Exemplary treatment options for hepatitis C (HCV) include interferons, e.g., interferon alfa-2b, interferon alfa-2a, and interferon alfacon-1. Less frequent interferon dosing can be achieved using pegylated interferon (interferon attached to a polyethylene glycol moiety which significantly improves its pharmacokinetic profile). Combination therapy with interferon alfa-2b (pegylated and unpegylated) and ribavarin has also been shown to be efficacious for some patient populations. Other agents currently being developed include RNA replication inhibitors (e.g., ViroPharma's VP50406 series), antisense agents, therapeutic vaccines, protease inhibitors, helicase inhibitors and antibody therapy (monoclonal and polyclonal).

The compounds and compositions of the present invention may also be used with agents that enhance the body's immune system, including low-dose cyclophosphamide, thymostimulin, vitamins and nutritional supplements (e.g., antioxidants, including vitamins A, C, E, beta-carotene, zinc, selenium, glutathione, coenzyme Q-10 and echinacea), and vaccines, e.g., the immunostimulating complex (ISCOM), which comprises a vaccine formulation that combines a multimeric presentation of antigen and an adjuvant.

The above-described methods find use in a variety of different applications, representative types of which are now described in greater detail below.

Utility

The subject methods find use in the treatment of a variety of different conditions in which the reduction of a target viral genome amount in a target cell or host comprising the same is desired. In many embodiments, the subject methods find use in the treatment of a host suffering from a viral mediated disease condition. By treatment is meant that at least an amelioration of the symptoms associated with the condition afflicting the host is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g. prevented from happening, or stopped, e.g. terminated, such that the host no longer suffers from the condition, or at least the symptoms that characterize the condition.

A variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

As indicated above, the methods may be employed for any viral genome whose abundance in a target cell correlates with a miRNA in that cell. In certain embodiments, the viral genome is a genome of virus having an RNA genome, where the virus may be from the family Flaviviridae, e.g., a hepacivirus, such as a hepatitis C virus, e.g., Hepatitis C virus (isolate 1), Hepatitis C virus (isolate BK), Hepatitis C virus (isolate EC1), Hepatitis C virus (isolate EC10), Hepatitis C virus (isolate HC-J2), Hepatitis C virus (isolate HC-J5), Hepatitis C virus (isolate HC-J6), Hepatitis C virus (isolate HC-J7), Hepatitis C virus (isolate HC-J8), Hepatitis C virus (isolate HC-JT), Hepatitis C virus (isolate HCT18), Hepatitis C virus (isolate HCT27), Hepatitis C virus (isolate HCV-476), Hepatitis C virus (isolate HCV-KF), Hepatitis C virus (isolate Hunan), Hepatitis C virus (isolate Japanese), Hepatitis C virus (isolate Taiwan), Hepatitis C virus (isolate TH), Hepatitis C virus isolate H, Hepatitis C virus type 1, Hepatitis C virus type 10, Hepatitis C virus type 2, Hepatitis C virus type 3, Hepatitis C virus type 4, Hepatitis C virus type 5, Hepatitis C virus type 6, Hepatitis C virus type 7, Hepatitis C virus type 8, etc.

In certain representative embodiments, the subject invention is employed in methods of treating a host suffering from an HCV mediated disease condition, e.g., non A, non-B hepatitis (NANBH). In these representative embodiments, an effective amount of a miR122 inhibitory agent, such as an antisense oligo as exemplified below, is administered to the host such that the amount of HCV genome present in the host cells, particularly liver cells, is reduced, as described above.

Pharmaceutical Compositions

Also provided are pharmaceutical compositions containing the miRNA inhibitory compounds employed in the subject methods. Accordingly, the compounds, e.g., in the form of a pharmaceutically acceptable salt, can be formulated for oral or parenteral administration for use in the subject methods, as described above.

By way of illustration, the compounds can be admixed with conventional pharmaceutical carriers and excipients (i.e., vehicles) and used in the form of aqueous solutions, tablets, capsules, elixirs, suspensions, syrups, wafers, and the like. Such pharmaceutical compositions contain, in certain embodiments, from about 0.1 to about 90% by weight of the active compound, and more generally from about 1 to about 30% by weight of the active compound. The pharmaceutical compositions may contain common carriers and excipients, such as corn starch or gelatin, lactose, dextrose, sucrose, microcrystalline cellulose, kaolin, mannitol, dicalcium phosphate, sodium chloride, and alginic acid. Disintegrators commonly used in the formulations of this invention include croscarmellose, microcrystalline cellulose, corn starch, sodium starch glycolate and alginic acid.

A liquid composition will generally consist of a suspension or solution of the compound or pharmaceutically acceptable salt in a suitable liquid carrier(s), for example, ethanol, glycerine, sorbitol, non-aqueous solvent such as polyethylene glycol, oils or water, with a suspending agent, preservative, surfactant, wetting agent, flavoring or coloring agent. Alternatively, a liquid formulation can be prepared from a reconstitutable powder.

For example, a powder containing active compound, suspending agent, sucrose and a sweetener can be reconstituted with water to form a suspension; and a syrup can be prepared from a powder containing active ingredient, sucrose and a sweetener.

A composition in the form of a tablet can be prepared using any suitable pharmaceutical carrier(s) routinely used for preparing solid compositions. Examples of such carriers include magnesium stearate, starch, lactose, sucrose, microcrystalline cellulose and binders, for example, polyvinylpyrrolidone. The tablet can also be provided with a color film coating, or color included as part of the carrier(s). In addition, active compound can be formulated in a controlled release dosage form as a tablet comprising a hydrophilic or hydrophobic matrix.

A composition in the form of a capsule can be prepared using routine encapsulation procedures, for example, by incorporation of active compound and excipients into a hard gelatin capsule. Alternatively, a semi-solid matrix of active compound and high molecular weight polyethylene glycol can be prepared and filled into a hard gelatin capsule; or a solution of active compound in polyethylene glycol or a suspension in edible oil, for example, liquid paraffin or fractionated coconut oil can be prepared and filled into a soft gelatin capsule.

Tablet binders that can be included are acacia, methylcellulose, sodium carboxymethylcellulose, poly-vinylpyrrolidone (Povidone), hydroxypropyl methylcellulose, sucrose, starch and ethylcellulose. Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used. Additionally, it may be desirable to add a coloring agent to make the dosage form more attractive in appearance or to help identify the product.

The compounds of the invention and their pharmaceutically acceptable salts that are active when given parenterally can be formulated for intramuscular, intrathecal, or intravenous administration.

A typical composition for intramuscular or intrathecal administration will be of a suspension or solution of active ingredient in an oil, for example, arachis oil or sesame oil. A typical composition for intravenous or intrathecal administration will be a sterile isotonic aqueous solution containing, for example, active ingredient and dextrose or sodium chloride, or a mixture of dextrose and sodium chloride. Other examples are lactated Ringer's injection, lactated Ringer's plus dextrose injection, Normosol-M and dextrose, Isolyte E, acylated Ringer's injection, and the like. Optionally, a co-solvent, for example, polyethylene glycol, a chelating agent, for example, ethylenediamine tetraacetic acid, and an antioxidant, for example, sodium metabisulphite may be included in the formulation. Alternatively, the solution can be freeze dried and then reconstituted with a suitable solvent just prior to administration.

The compounds of the invention and their pharmaceutically acceptable salts which are active on rectal administration can be formulated as suppositories. A typical suppository formulation will generally consist of active ingredient with a binding and/or lubricating agent such as a gelatin or cocoa butter or other low melting vegetable or synthetic wax or fat.

The compounds of this invention and their pharmaceutically acceptable salts which are active on topical administration can be formulated as transdermal compositions or transdermal delivery devices ("patches"). Such compositions include, for example, a backing, active compound reservoir, a control membrane, liner and contact adhesive. Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference in its entirety. Such patches may be constructed for continuous, pulsatile, or on demand delivery of pharmaceutical agents.

Optionally, the pharmaceutical composition may contain other pharmaceutically acceptable components, such a buffers, surfactants, antioxidants, viscosity modifying agents, preservatives and the like. Each of these components is well-known in the art. See, for example, U.S. Pat. No. 5,985,310, the disclosure of which is herein incorporated by reference.

Other components suitable for use in the formulations of the present invention can be found in Remington's Pharmaceutical Sciences, Mace Publishing Company, Philadelphia, Pa., 17th ed. (1985). In an embodiment, the aqueous cyclodextrin solution further comprise dextrose, e.g., about 5% dextrose.

Kits

Also provided are reagents and kits thereof for practicing one or more of the above-described methods. The subject reagents and kits thereof may vary greatly. Typically, the kits at least include a miRNA inhibitory agent as described above. The kits may also include a pharmaceutically acceptable delivery vehicle, which may be combined with or separate from the miRNA inhibitory agent in the kit, e.g., where the two components may be in the same or separate containers in the kit.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

Systems

Also provided are systems that find use in practicing the subject methods, as described above. For example, systems for practicing the subject methods may include one or more pharmaceutical formulations, which include the miRNA inhibitory agent. The term "system" as employed herein refers to a collection of components, e.g., active agent, delivery vehicle, etc, present in a single composition or as disparate compositions, that are brought together for the purpose of practicing the subject methods. For example, separately obtained active agent and delivery vehicle brought together and coadministered to a subject, according to the present invention, are a system according to the present invention.

The following examples are offered by*way of illustration and not by way of limitation.

EXPERIMENTAL

I. Results & Discussion

To begin to understand the roles of miR-122 in regulating mRNA function, we monitored the expression of miR-122 in RNA samples extracted from liver tissues and liver cell lines. FIG. 1A shows that miR-122 could be detected in mouse and human liver, and in cultured human liver Huh7 cells, but not in human cervical carcinoma-derived HeLa cells, or even in human liver-derived HepG2 cells (FIG. 1A).

Figure 1B:
Figure 1C:
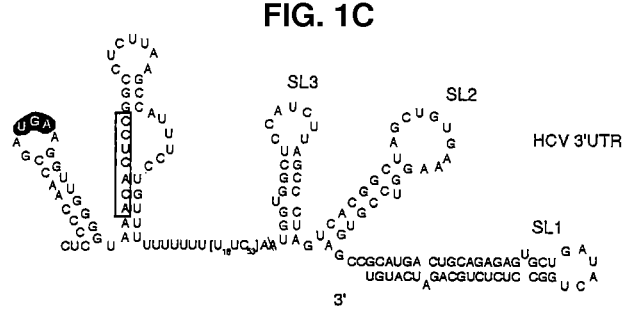
Figure 1C:
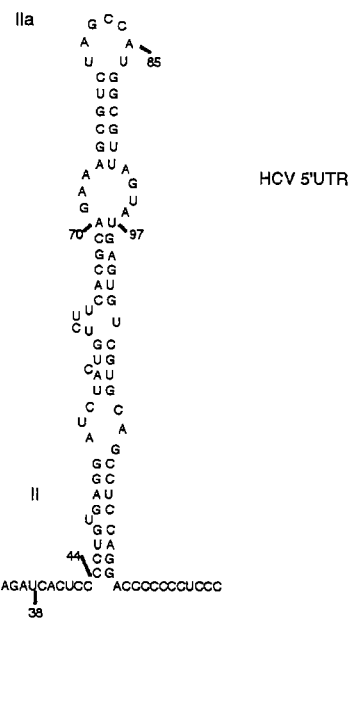

It is known that hepatitis C virus (HCV) RNA that carries adaptive mutations can replicate in Huh7 but not in HepG2 cells, and we wanted to explore whether the presence of miR-122 in HCV RNA-replicating Huh7 cells was more than pure coincidence. To this end, we inspected the 9,600 nucleotide positive-strand viral RNA genome for potential miR-122 binding sites that would fulfill the rules for a successful miRNA-target mRNA interaction. We searched for sequences in the viral mRNA that could engage in perfect Watson and Crick base pairing with nucleotides 2 through 8, the "seed sequence" of miR-122. Using this rule, we noted two predicted binding sites for miR-122 (FIG. 1B) in the viral non-coding regions. One was located in the variable region of the viral 3' noncoding region of the type 1a genotype (FIG. 1C). Although this sequence was in the nominally "variable region", inspection of all six HCV genotypes revealed that the seed match sequence itself was highly conserved (Table 1). The second miR-122 binding site was predicted to reside in the 5' noncoding region, only 21 nucleotides from the 5' end of the viral genome (FIG. 1C). Here, the putative seed match sequence was flanked by an adenosine residue. This leads to further base pairing with nucleotide 1 in the miRNA, which is in most cases a uridine residue, resulting in increased specificity of microRNA-target interactions. The putative seed match sequence for miR-122, including the flanking adenosine residue, is highly conserved among all viral genotypes with the exception of the seed match sequence in genotype 2 which lacks the anchoring adenosine (Table 1).

TABLE 1

| Genotype SEQ ID NO: | 5'UTR | 3'UTR |
|---|---|---|
| 1a (01 & 02) | UGAUGGGGCGACACUCCAC | UGAAGGUUGGGGUAACACUCCGGCC |
| 1b (03 & 04) | AUUGGGGGCGACACUCCACC | UGAACGGGGAGCUAAACACUCCAGG |
| 2 (05 & 06) | AAUAGGGGCGACACUCCGCC | UAGAGCGGCACACACUAGGUACACUCCA |
| 3 (07 & 08) | UACGAGGCGACACUCCACCA | UGAGCUGGUAAGAUAACACUCCAUU |
| 4 (09 & 10) | UAUGAGAGCAACACUCCACC | UAGGCAGCUUAACACUCCGACCUUA |
| 5 (11 & 12) | UAUUGGGGCGACACUCCACC | UAGGCUGGGAGCUAAACACUCCAUA |
| 6 (13 & 14) | AAUGGGGCGACACUCCACCA | UAGACAGGGAGCAUAAAUAACACUCCA |

The predicted miR-122 binding sites in HCV are conserved in all genotypes. The sequence of the 5'UTR from nucleotides 10-30 in the genome, and of the 3'UTR from the stop codon to the end of the predicted binding site, is shown for each genotype. The seed matches are indicated in bold type.

Figure 2A:
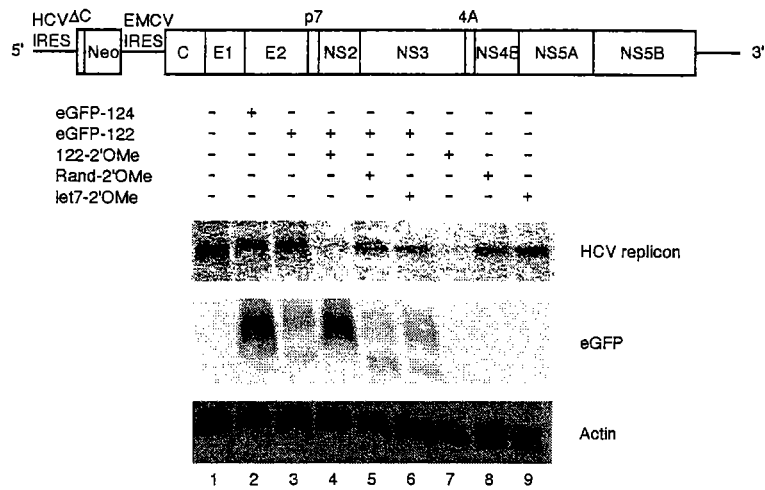
FIGS. 2A-C. Sequestration of miR-122 reduces HCV RNA and protein abundance in replicon cells. (A) Northern blot analysis of replicon, eGFP and actin RNA in the NNeo/C-5B replicon cell line. The organization of the replicon is indicated. The eGFP sensor plasmids and 2'-O-methyl oligonucleotides were introduced into cells by lipofectamine 2000-mediated transfection, and total RNA was extracted 48 hours later. eGFP-124 and eGFP-122 are eGFP expression vectors with complementary sites for miR-124 and miR-122, respectively, in the 3'UTR. 122-2'OMe is a 31mer 2'-O-methylated oligomer complementary to miR-122, Rand-2'OMe is a randomized version of this sequence, and let7-2'OMe is a similar oligomer complementary to let-7a. (B) Western blot showing levels of HCV core protein, eGFP and actin 48 hours post transfection with the indicated eGFP sensor plasmids and 2'-O-methylated oligomers. (C) Northern analysis of replicon, eGFP and actin RNA in Huh7 cells containing the genome-length genotype 1a replicon H77c and transfected with eGFP-122 and 122-2'OMe.

To determine whether miR-122 played a functional role in regulating HCV gene expression we tested whether the accumulation of replicon RNAs would be affected when miR-122 was inactivated in NNeo/C-5B Huh7 cells (Ikeda, M. Yi, K. Li, S. M. Lemon, J. Virol. 76, 2997 (2002)). These cells constitutively express dicistronic viral replicons, in which the HCV internal ribosome entry site (IRES) directs the synthesis of the neomycin resistance gene product and the encephalomyocarditis viral IRES directs the synthesis of the structural and nonstructural proteins of the HCV-N 1b strain (FIG. 2A, top diagram). To inactivate miR-122 in this cell line, NNeo/C-5B cells were transfected with a 2'-O-methylated RNA oligonucleotide (122-2'OMe), 31 nucleotides in length, with exact complementarity to miR-122; 2'O-methylated complementary RNA nucleotides have been shown to sequester miRNAs (Hutvagner, et al., PLoS Biol. 2, E98 (2004); Meister, et al., RNA 10, 544 (2004)). As a control for functional inactivation of miR-122 we monitored the expression of eGFP sensor mRNAs (eGFP-122) that contained sequences complementary to miR-122 in their 3' noncoding regions. Due to its complete complementarity, miR-122 should function as an siRNA on these target molecules and lead to their nucleolytic degradation. Indeed, little full-length eGFP-122 RNA was visible in cells transfected with plasmids encoding eGFP-122 (FIG. 2A, lane 3), although a similar RNA that contained sites complementary to the brain-specific miR-124 was expressed at high levels (FIG. 2A, lane 2). Upon transfection with 122-2'OMe, the amount of eGFP-122 RNA dramatically increased (FIG. 2A, lane 4), whereas a randomized version of this oligomer (Rand-2'OMe, lane 5) or an oligomer complementary to the miRNA let-7a (let7-2'OMe) had no effect (FIG. 2A, lane 6). A 23mer oligomer complementary to miR-122 had the same effect as the 31mer.

Figure 2B:
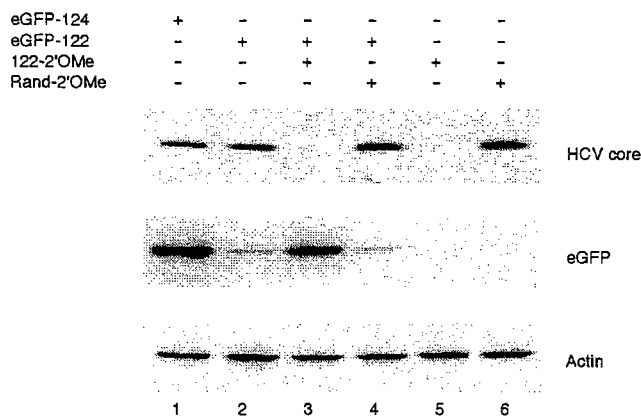

Surprisingly, the level of HCV viral replicon RNA was specifically and dramatically reduced when miR-122 was inactivated (FIG. 2A, lanes 4 and 7). Reduced viral mRNA abundance resulted in a decrease in HCV protein expression in cells transfected with the 122-2'OMe oligomer, while the level of eGFP sensor protein increased under this experimental condition (FIG. 2B, lane 3). It was possible that the 122-2'OMe oligomers affected replicon RNA and protein levels by interacting with the negative strand of HCV, which has considerable complementarity to the oligomer sequence in the region surrounding the predicted miR-122 binding sites. However, an oligomer with exact complementarity to the negative strand in the 3' noncoding region encompassing the predicted miR-122 binding site had no effect on replicon level, suggesting that the viral negative strand is not accessible to the oligomer. Furthermore, the 122-2'OMe oligomer did not affect total protein synthesis in transfected cells, excluding the possibility that the 122-2'OMe oligomer induced antiviral effects. Overall, these findings indicate that miR-122 is essential to maintain intracellular abundance of HCV replicon RNAs.

Figure 2C:
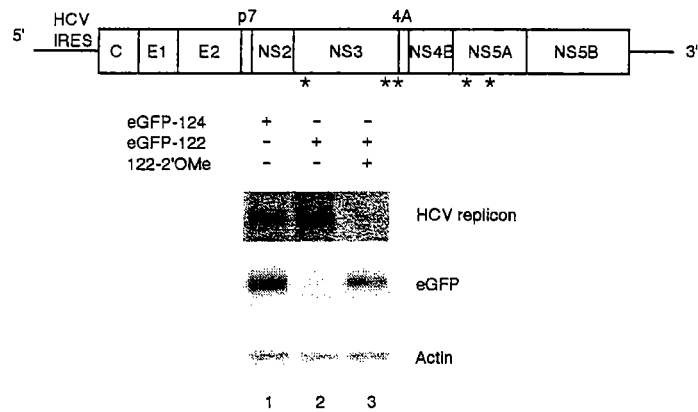

To determine whether miR-122 would affect RNA accumulation in cells newly transfected with replicating HCV RNAs, RNA transcripts were synthesized from a cDNA that encodes a full-length genotype 1a strain H77c genome with five adaptive mutations (FIG. 2C, top diagram) that allow high levels of RNA replication in Huh7 cells (Yi & Lemon, J. Virol. 78, 7904 (2004)). Introduction of these RNA molecules into Huh7 cells led to accumulation of viral RNA in the presence of endogenous miR-122 (FIG. 2C, lanes 1 and 2); in contrast, viral RNA failed to accumulate when miR-122 was sequestered by 122-2'OMe oligomers (FIG. 2C, lane 3). Thus, miR-122 is required to maintain HCV RNA abundance of both genotypes 1a and 1b, in stably expressing cell lines and upon direct transfection.

Figure 3A:
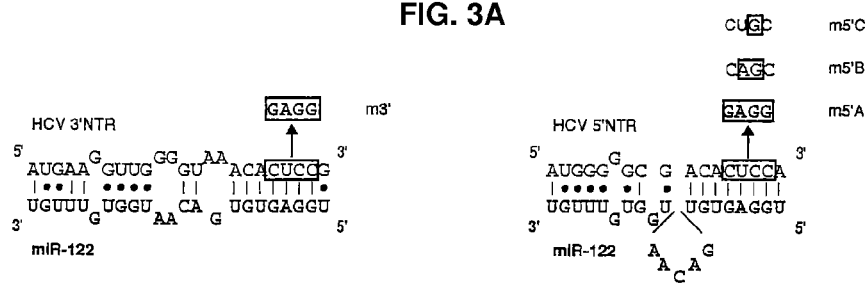
FIGS. 3A-3C. The predicted miR-122 binding site in the 5'noncoding region of HCV is required for viral RNA maintenance due to a direct interaction with miR-122 (A) Position of the mutations introduced into the H77c full-length RNA. A 4 nt substitution mutation was introduced into the seed match in the 3' noncoding region (m3') and 4 nt, 2 nt or 1 nt substitution mutations into the 5' noncoding region seed match (m5'A, B and C respectively). The mutated nucleotides are enclosed in boxes. (B) RNA was synthesized by in vitro transcription and introduced into Huh7 cells by electroporation, and replicon RNA levels were determined by Northern blotting 5 days later. Methylene blue staining of ribosomal RNA as a loading control is shown. (C) Huh7 cells were transfected with synthetic duplexes corresponding to wild-type miR-122 (122wt) or miR-122 with a 1 nt mutation in the seed complementary to the m5'C seed match mutation (122mC), with the opposite strand of the duplex based on the miR-122 precursor hairpin. The duplexes were introduced into Huh7 cells one day prior to electroporation with wildtype H77c RNAs or mutant m5'C RNAs, and again at 1 and 3 days post electroporation. Total RNA was harvested 5 days post electroporation and replicon and actin RNA levels determined by Northern blotting.
Figure 3B:
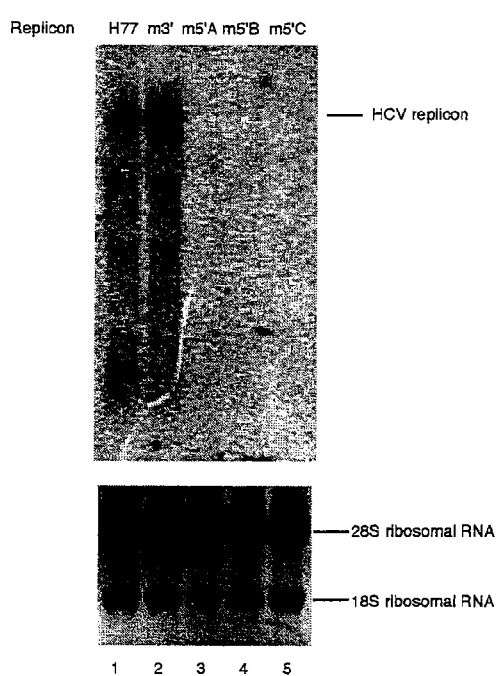

To determine whether the putative miR-122 binding sites were required for the miR-122 effects on RNA accumulation, mutations were introduced into the full-length H77c cDNA. Transfection of H77c RNAs containing a four-nucleotide substitution mutation in the predicted seed match in the 3' noncoding region (FIG. 3A), which should abolish miR-122 binding, did not diminish RNA accumulation (FIG. 38, lane 2). In contrast, a four-nucleotide substitution mutation in the predicted seed match in the 5' noncoding region (FIG. 3A) failed to induce RNA accumulation (FIG. 3B, lane 3). Strikingly, genomes that contained a two-nucleotide (FIG. 3B, lane 4) or even a single-nucleotide (FIG. 3B, lane 5) substitution mutation at position 27 in the viral genome (m5'C) also failed to accumulate five days after transfection. These findings indicate either that failure to recruit miR-122 resulted in loss of viral RNA, or that the mutations had some effect on RNA replication or stability.

Figure 3C:
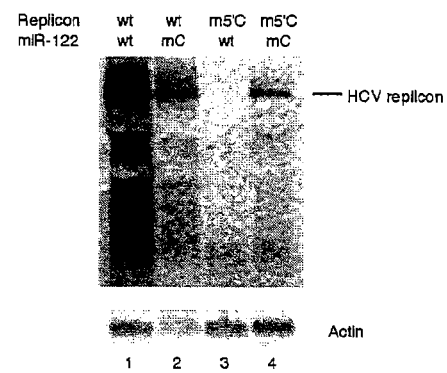

If mutations in the miR-122 seed sequence reduced RNA accumulation due to poor binding of miR-122, ectopic expression of miR-122 RNAs that contained a mutation at the third nucleotide from the 5' end (mC) should restore the formation of miR-122(mC)-m5'C RNA complexes (Lewis, et al., Cell 120, 15 (2005)). Ectopic expression of wildtype miR-122 RNAs did not rescue m5'C-containing mutated viral RNAs (FIG. 3C, lane 3), but enhanced the abundance of wildtype viral RNAs (FIG. 30C, lane 1) and replicon RNAs (FIGS. S3A & B), demonstrating that the introduced miR-122 RNAs were processed to functional single-stranded miR-122 RNA molecules and that the endogenous pool of miR-122 that mediates the accumulation of viral RNA is limiting. In contrast, expression of mutated m5'C miR-122 duplexes allowed accumulation of m5'C-containing viral RNAs (FIG. 3C, lane 4), strongly arguing for a genetic interaction between miR-122 and the 5' terminal sequences of the HCV genome. Furthermore, the rescue of mutated m5'C-containing viral RNAs by mutated mC-miR-122s must be due to a direct HCV RNA-miR-122 interaction, rather than an indirect effect via another, probably cellular, miR-122 target.

Figure 4:
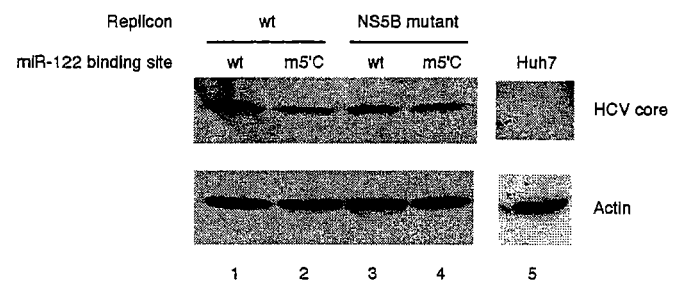
FIG. 4-Mutation of the miR-122 binding site does not affect HCV mRNA translation. The m5'C mutation was introduced into a replication-deficient mutant of H77c, AAG-H77, containing amino acids changes GDD to AAG at positions 2737 to 2739 in the viral polymerase NS5B (23). Lysates were harvested 20 hours after transfection of the replicon RNA, and HCV core protein and actin expression determined by Western blotting.
Figure 5A:
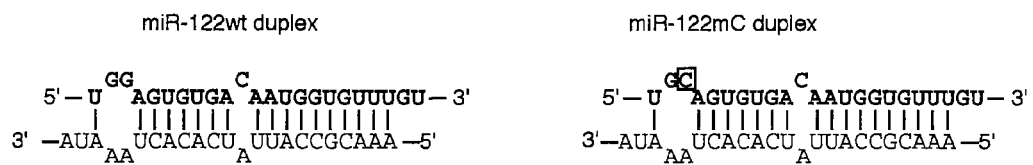
FIGS. 5A and B
Figure 5B:
FIG. 5B presents data showing that addition of synthetic miR-122 duplex to NNeo/C-5B replicon cells results in an increase in replicon RNA abundance. The indicated eGFP sensor plasmids and wild-type (122wt) or mutant (122mC) miR-122 duplexes were introduced into cells by transfection using lipofectamine 2000. Total RNA was extracted 48 hours later and replicon, eGFP and actin RNA levels determined by Northern blotting.
Figure 5B:
Figure 5B:

We next examined whether miR-122 modulates translation of HCV RNA, known to occur by an unusual internal ribosome entry mechanism (Ji, et al., Proc. Natl. Acad. Sci. USA 101, 16990 (2004); Otto, Cell 119, 369 (2004); Pestova, et al., Genes Dev. 12, 67 (1998)). Specifically, we monitored the production of HCV core protein from replicating and non-replicating viral RNAs in the presence or absence of a functional miR-122 binding site. FIG. 4 shows that similar amounts of core protein accumulated in cells transfected with wildtype (lane 1) or m5'C-mutant RNAs (lane 2) at twenty hours after transfection, a time point at which little RNA replication should have taken place. To test directly whether core was synthesized from input RNAs, translation of replication-defective viral RNAs was examined. Results showed that wildtype (FIG. 4, lane 3) and m5'C-mutant (lane 4) input RNAs were translated with similar efficiencies, indicating that miR-122 regulates HCV RNA abundance at a step subsequent to translation, most likely at the RNA replication step.

Our finding that the HCV genome recruits miR-122 to its 5' end is novel. Our finding demonstrates that miR 122 is a target for controlling levels of HCV, and therefore a target for treating HCV mediated disease conditions.

II. Materials & Methods a. Oligonucleotides and DNA Constructs

RNA oligonucleotides and 2'-O-methylated oligonucleotides were synthesized by Dharmacon Inc. (Lafayette, Colo.). The sequences were: 122-2'OMe, 5'AGACACAAA-CACCAUUGUCACACUCCACAGC (SEQ ID NO:15); Rand-2'OMe, 5'CACGUUAAAACCAUACGCACUAC-GAAACCCC (SEQ ID NO:16); let7-2'OMe, 5'CUAAAAC-UAUACAACCUACUACCUCAUCCCA (SEQ ID NO:17); 122-2'OMe23, 5'ACAAACACCAUUGUCACACUCCA (SEQ ID NO:18); HCVbs-2'OMe, 5'UGAACGGGGAGC-UAAACACUCCA ((SEQ ID NO:19); miR-122wt, 5'UGGAGUGUGACAAUGGUGUUUGU ((SEQ ID NO:20); miR-122mC, 5'UGCAGUGUGACAAUGGUGU-UUGU (SEQ ID NO:21); miR-122*, 5'AAACGCCAUUAU-CACACUAAAUA ((SEQ ID NO:22). Duplexes were formed between the wt or mC forms of miR-122 and miR-122*. The miR-122 sensor plasmid eGFP-122 was constructed by PCR-mediated insertion of the sequence 5'ACAAACACCAUU-GUCACACUCCA (SEQ ID NO:23), which has exact complementarity to miR-122, at the Not I restriction site in the 3'noncoding region of plasmid pd2eGFP-N1 (Clontech). To construct the control vector eGFP-124, the sequence 5'TTAAGGCACGCGGTGAATGCCA (SEQ ID NO:24), which is complementary to the brain-specific miR-124, was inserted. Substitution mutations were introduced into the 3' and 5'noncoding regions of the H77c replicon vector (YI & Lemon, J Virol 78, 7904 (August, 2004)) by overlap PCR using mutagenic primers, and subsequent ligation of the PCR products into the parent vector.

B. Cell Culture and Transfection

The Huh7, HeLa and HepG2 cell lines were cultured in DMEM supplemented with 10% FBS and 1% non-essential amino acids (Gibco). The Huh7 cell line containing the dicistronic replicon NNeo/C-5B has been described previously (Ikeda, et al., J Virol 76, 2997 (March, 2002)) and was maintained in the presence of 1 mg/ml G418. In vitro transcribed H77c genomic RNA was introduced into Huh7 cells by electroporation as described in Yi & Lemon, supra, and RNA was prepared and processed 5 days later. To observe protein synthesis from replication-deficient H77c RNA, Dmrie-C (Invitrogen) was used to deliver RNA into Huh7 cells, and protein-lysates were prepared and processed 20 hours later. This method was used because electroporated cells are not fully adherent at such early timepoints. DNA constructs and oligonucleotides were introduced into cells using lipofectamine 2000 (Invitrogen), according to the manufacturer's instructions. The 2'-O-methylated oligonucleotides and the miR-122 RNA duplexes were delivered at a concentration of 50 nM into cells in 6-well plates. Transfected cells were cultured for 48 hours before harvesting.

C. RNA Isolation and Northern Blotting

Total RNA was extracted from cells using Trizol reagent (Invitrogen), according to the manufacturer's instructions. To detect miRNA expression, 30 µg of total RNA was separated on 15% polyacrylamide gels containing 7M urea in 0.5×TBE, transferred to Hybond N+ membrane (Amersham), and hybridized to a 5' $^{32}$P-labelled oligonucleotide complementary to miR-122 with the sequence 5'ACAAACACCAUU-GUCACACUCCA (SEQ ID NO:25). To analyse mRNA levels, 2.5 µg of RNA from the NNeo/C-5B replicon cells, or 15±g of RNA from cells transfected with H77c RNA, was separated in 1% agarose gels containing 1×MOPS buffer and 2.2M formaldehyde, and transferred to Zeta-probe membrane (Bio-Rad). The membranes were hybridized in ExpressHyb (Clontech) to random-primed $^{32}$P-labelled DNA probes corresponding to nucleotides 84-374 of HCV, 40-814 of eGFP, and 685-1171 of α-actin as indicated.

D. Western Blotting and Metabolic Labelling

Protein samples were obtained by scraping cells into RIPA containing a complete protease inhibitor cocktail (Roche). 10 µg of protein was separated by 12% SDS-PAGE and transferred to Immobilon-P membrane (Millipore). Membranes were probed with antibody 6G7 directed against the HCV core protein (a kind gift of Harry Greenberg, Stanford University), or antibodies dirceted against eGFP (Roche) or actin (Sigma). For metabolic labelling, cells were incubated in methionine-free medium for 1 hour before incubation with $^{35}$S-methionine for 1 hour and extraction of protein. 25 µg of protein was precipitated using trichloroacetic acid and $^{35}$S-methionine incorporation was quantitated by filter binding.

E. Sequence Data

Sequences of 5' and 3'noncoding regions of different HCV genotypes were obtained from the HCV database, located at the web site produced by placing "http://" before and ".gov" after "hcv.lanl" and representative examples of each genotype are shown in Table 1. The strains were: H77c (genotype 1a), GenBank accession no. AF011751; HCV-N (1b), AF139594; JFH-1 (2a), AB047639; NZL1 (3a), D17763; HEMA51 (4a), D45193 and D45194; FR741 (5a), D50466 and D50467; TH271 (6f), D37848 and D37858.

It is evident from the above results and discussion that the subject invention provides for new ways of treating viral mediated disease conditions, such as HCV mediated disease conditions. As such, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A pharmaceutical composition comprising: a) an antisense oligonucleotide complementary to miR-122 such that said antisense oligonucleotide binds to miR-122 and inhibits its activity, wherein the antisense oligonucleotide comprises a nucleotide sequence of SEQ ID NO:15; and b) a pharmaceutically acceptable carrier; wherein said composition is prepared by a method of i) providing said antisense oligonucleotide as a powder, and ii) reconstituting said powder into a liquid form with said pharmaceutically acceptable carrier.

2. The pharmaceutical composition of claim 1, wherein said pharmaceutically acceptable carrier is sterile water.

3. The pharmaceutical composition of claim 1, wherein the antisense oligonucleotide complementary to miR-122 comprises a 2'-O-methyl modification.

4. The pharmaceutical composition of claim 1, wherein said composition comprises 0.1 to 90% by weight said antisense oligonucleotide.

5. The pharmaceutical composition of claim 1, wherein said composition comprises 1 to 30% by weight said antisense oligonucleotide.

6. The pharmaceutical composition of claim 1, wherein said composition is formulated for parenteral administration.

7. The pharmaceutical composition of claim 6, wherein said parenteral administration comprises intravenous administration.

* * * * *